(12) United States Patent
Jung et al.

(10) Patent No.: US 6,500,647 B1
(45) Date of Patent: Dec. 31, 2002

(54) RECOMBINANT EXPRESSION VECTOR OF HUMAN PARATHYROID HORMONE

(75) Inventors: Eun-Kyung Jung, Seoul (KR); Doo-Hong Park, Seoul (KR); Soo-Il Chung, Sungnam-si (KR)

(73) Assignee: Mogam Biotechnology Research Institute, Kyonggi-Do (KR)

( * ) Notice: Subject to any disclaimer, the term of this patent is extended or adjusted under 35 U.S.C. 154(b) by 0 days.

(21) Appl. No.: 09/463,282

(22) PCT Filed: Jun. 5, 1998

(86) PCT No.: PCT/KR98/00146

§ 371 (c)(1),
(2), (4) Date: Jan. 20, 2000

(87) PCT Pub. No.: WO99/05277

PCT Pub. Date: Feb. 4, 1999

(30) Foreign Application Priority Data

Jul. 25, 1997 (KR) ............................................. 97-35230

(51) Int. Cl.[7] ........................ C12N 15/09; C07H 21/04; C12P 21/00; C08H 1/00; C07K 17/00
(52) U.S. Cl. .................... 435/69.7; 536/23.5; 536/23.1; 536/23.4; 536/24.1; 536/24.2; 435/69.1; 435/320.1; 435/35; 435/252.33; 435/69.4
(58) Field of Search ................ 536/23.5, 24.1, 536/24.2, 23.4, 23.1; 435/320.1, 69.1, 35, 252.1, 69.4, 252.33, 69.7; 424/130.1; 530/23.51, 399, 402

(56) References Cited

PUBLICATIONS

Smith, T.F. and Zhang, X. (1997) The challenges of genome sequence annotation or "The devil is in the details", Nature Biotechnology, 15: 1222–1223.*
Brenner, S. (1999) Errors in genome annotation, Trends in Genetics, 15(4): 3–4, esp. Fig. 2.*
Charlier, H.A., et al., Biochemistry, 1994, 33:9343–9350.
Chung, B. H., et al., Korea Research Institute of Bioscience and Biotechnology, 1997, 5(3):106–110.
Gardella, T. J. et al., The Journal of Biological Chemistry, 1990, 265(26): 15854–15859.
Hallenbeck, P.L. et al., Journal of Bacteriology, 1987, 169(8):3669–3678.
Harder, M.P.F. et al., Appl. Microbiol. Biotecnol., 1993, 39:329–334.
Hendy, G. et al., Proc. Natl. Acad. Sci., 1981, 78(12):7365–7369.
Hogset, A., et al., The Journal of Biological Chemistry, 1990, 265(13):7338–7344.
Kareem, B.N., et al., Analytical Biochemistry, 1992, 204:26–33.
Oldenburg, K. R., et al., Protein Expression and Purification, 1994, 5:278–284.
Oshika, Y., et al., Int. J. Peptide Protein Res., 1994, 43:441–447.
Rabbani, S. A., et al., Biochemistry, 1990, 29(43):10080–10089.
Sung, W.L., et al., The Journal of Biological Chemistry, 266(5):2831–2835.

* cited by examiner

Primary Examiner—Elizabeth Kemmerer
Assistant Examiner—Sandra Wegert

(57) ABSTRACT

The present invention relates to a recombinant expression vector which is prepared by inserting a human parathyroid hormone gene containing a urokinase-specific cleavage site into an L-arabinose inducible vector containing a phosphoribulokinase gene fragment of *Rhodabacter sphaeroides* or its mutated gene as a fusion partner, or its mutate gene as a fusion partner, a recombinant microorganism transformed with the said expression vector, and a process for preparing human parathyroid hormone on a large scale by cultivating the said microorganism in a medium containing L-arabinose. In accordance with the invention, a recombinant human PTH having the same activity of the native human PTH can be prepared in a high yield through the precise control of induction by a manufacturing process which comprises a step of inducing expression of fusion protein in the microorganism transformed with the recombinant expression vector by L-arabinose.

14 Claims, 16 Drawing Sheets

1 : 5' GGGGAGTACTGCAGCTGGATCC<u>GGTACTGGTAGA</u>
                                            UK Cleavage Recognition Site

2 : 5' TCTACCAGTACCGGATCCAGCTGCAGTACTCCCC

3 : 5' TCTGTTTCGGAAATCCAGCTTATGCATAACCTGGGTAAACA

4 : 5' CGAGTTCAGATGTTTACCCAGGTTATGCATAAGCTGGATTTCCGAAACAGA

5 : 5' TCTGAACTCGATGGAACGTGTTGAATGGCTGCGTAAAAAACTGCA

6 : 5' GTTTTTTACGCAGCCATTCAACACGTTCCAT

7 : 5' GGATGTTCATAACTTCGTTGCGCTGGGGGCTCCACTGGC

8 : 5' TCGCGCGGCGCCAGTGGAGCCCCCAGCGCAACGAAGTTATGAACATCCTGCA

9 : 5' GCCGCGCGAAGGCGGGTTCGCAGCGCCCACGTAAAAAGGAAGATAA

10 : 5' TACCAGAACGTTATCTTCCTTTTTACGTGGGCGCTGCTAACCCGCA

11 : 5' CGTTCTGGTAGAGTCGCATGAAAAGTCTCTTGGCGAGGCTGATAA

12 : 5' TACGTCTGCTTTATCAGCCTCGCCAAGAGACTTTTCATGCGACTC

13 : 5' AGCAGACGTAAACGTTTTGACTAAAGCAAAATCTCAATAATGAT
                                                                  <u>stop</u>

14 : 5' CTAGATCATTATTGAGATTTTGCTTTAGTCAAAACGTT

FIG. 2

SEQUENCE LISTING

```
<160> NUMBER OF SEQ ID NOS: 26

<210> SEQ ID NO 1
<211> LENGTH: 34
<212> TYPE: DNA
<213> ORGANISM: Homo sapiens

<400> SEQUENCE: 1
ggggagtact gcagctggat ccggtactgg taga                          34

<210> SEQ ID NO 2
<211> LENGTH: 34
<212> TYPE: DNA
<213> ORGANISM: Homo sapiens

<400> SEQUENCE: 2
tctaccagta ccggatccag ctgcagtact cccc                          34

<210> SEQ ID NO 3
<211> LENGTH: 41
<212> TYPE: DNA
<213> ORGANISM: Homo sapiens

<400> SEQUENCE: 3
tctgtttcgg aaatccagct tatgcataac ctgggtaaac a                  41

<210> SEQ ID NO 4
<211> LENGTH: 51
<212> TYPE: DNA
<213> ORGANISM: Homo sapiens

<400> SEQUENCE: 4
cgagttcaga tgtttaccca ggttatgcat aagctggatt tccgaaacag a       51

<210> SEQ ID NO 5
<211> LENGTH: 45
<212> TYPE: DNA
<213> ORGANISM: Homo sapiens

<400> SEQUENCE: 5
tctgaactcg atggaacgtg ttgaatggct gcgtaaaaaa ctgca              45

<210> SEQ ID NO 6
<211> LENGTH: 31
<212> TYPE: DNA
```

-continued

<213> ORGANISM: Homo sapiens

<400> SEQUENCE: 6 gtttttacg cagccattca acacgttcca t                           31

<210> SEQ ID NO 7
<211> LENGTH: 39
<212> TYPE: DNA
<213> ORGANISM: Homo sapiens

<400> SEQUENCE: 7
ggatgttcat aacttcgttg cgctgggggc tccactggc                  39

<210> SEQ ID NO 8
<211> LENGTH: 52
<212> TYPE: DNA
<213> ORGANISM: Homo sapiens

<400> SEQUENCE: 8
tcgcgcggcg ccagtggagc ccccagcgca acgaagttat gaacatcctg ca   52

<210> SEQ ID NO 9
<211> LENGTH: 46
<212> TYPE: DNA
<213> ORGANISM: Homo sapiens

<400> SEQUENCE: 9
gccgcgcgaa ggcgggttcg cagcgcccac gtaaaaagga agataa          46

<210> SEQ ID NO 10
<211> LENGTH: 46
<212> TYPE: DNA
<213> ORGANISM: Homo sapiens

<400> SEQUENCE: 10
taccagaacg ttatcttcct ttttacgtgg gcgctgctaa cccgca          46

<210> SEQ ID NO 11
<211> LENGTH: 45
<212> TYPE: DNA
<213> ORGANISM: Homo sapiens

<400> SEQUENCE: 11
cgttctggta gagtcgcatg aaaagtctct tggcgaggct gataa           45

<210> SEQ ID NO 12
<211> LENGTH: 45
<212> TYPE: DNA
<213> ORGANISM: Homo sapiens

<400> SEQUENCE: 12
tacgtctgct ttatcagcct cgccaagaga cttttcatgc gactc           45

<210> SEQ ID NO 13
<211> LENGTH: 44
<212> TYPE: DNA
<213> ORGANISM: Homo sapiens

<400> SEQUENCE: 13
agcagacgta aacgttttga ctaaagcaaa atctcaataa tgat            44

<210> SEQ ID NO 14
<211> LENGTH: 38

```
<212> TYPE: DNA
<213> ORGANISM: Homo sapiens

<400> SEQUENCE: 14
ctagatcatt attgagattt tgctttagtc aaaacgtt                              38

<210> SEQ ID NO 15
<211> LENGTH: 15
<212> TYPE: DNA
<213> ORGANISM: Salmonella typhimurium

<400> SEQUENCE: 15
gccatcgtct tactc                                                      15

<210> SEQ ID NO 16
<211> LENGTH: 14
<212> TYPE: DNA
<213> ORGANISM: Salmonella typhimurium

<400> SEQUENCE: 16
gcgtttcagc catg                                                       14

<210> SEQ ID NO 17
<211> LENGTH: 6
<212> TYPE: DNA
<213> ORGANISM: Artificial Sequence
<220> FEATURE:
<223> OTHER INFORMATION: restriction site

<400> SEQUENCE: 17 catatg                                                                 6

<210> SEQ ID NO 18
<211> LENGTH: 8
<212> TYPE: DNA
<213> ORGANISM: Artificial Sequence
<220> FEATURE:
<223> OTHER INFORMATION: araB promoter

<400> SEQUENCE: 18 taaggagg                                                               8

<210> SEQ ID NO 19
<211> LENGTH: 23
<212> TYPE: DNA
<213> ORGANISM: Rhodobacter sphaeroides

<400> SEQUENCE: 19
ggagctgaat acatatgagc aag                                             23

<210> SEQ ID NO 20
<211> LENGTH: 22
<212> TYPE: DNA
<213> ORGANISM: Rhodobacter sphaeroides

<400> SEQUENCE: 20
cccccgggtc tagatcaggc ca                                              22

<210> SEQ ID NO 21
<211> LENGTH: 27
<212> TYPE: DNA
<213> ORGANISM: Rhodobacter sphaeroides

<400> SEQUENCE: 21
```

-continued

```
ggtgaaggat ccgggcgcca cgccggt                                               27

<210> SEQ ID NO 22
<211> LENGTH: 27
<212> TYPE: DNA
<213> ORGANISM: Rhodobacter sphaeroides

<400> SEQUENCE: 22
cggaacggat ccgatcttga ggtcggc                                               27

<210> SEQ ID NO 23
<211> LENGTH: 35
<212> TYPE: DNA
<213> ORGANISM: Rhodobacter sphaeroides

<400> SEQUENCE: 23
ccttgacccc ctcgcscacg aagatctggt cgaac                                      35

<210> SEQ ID NO 24
<211> LENGTH: 34
<212> TYPE: DNA
<213> ORGANISM: Rhodobacter sphaeroides

<400> SEQUENCE: 24
gcccgccgca tagcscacgt ccagctcggc cttc                                       34

<210> SEQ ID NO 25
<211> LENGTH: 36
<212> TYPE: DNA
<213> ORGANISM: Rhodobacter sphaeroides

<400> SEQUENCE: 25
gacgtaggtc cscgtcaccc cctgcccggt ctcgcc                                     36

<210> SEQ ID NO 26
<211> LENGTH: 258
<212> TYPE: DNA
<213> ORGANISM: Homo sapiens

<400> SEQUENCE: 26
tctgtttcgg aaatccagct tatgcataac ctgggtaaac atctgaactc gatggaacgt           60
gttgaatggc tgcgtaaaaa actgcaggat gttcataact tcgttgcgct gggggctcca          120
ctggcgccgc gcgaggcggg ttcgcagcgc ccacgtaaaa aggaagataa cgttctggta          180
gagtcgcatg aaaagtctct tggcgaggct gataaagcag acgtagacgt tttgactaaa          240
gcaaaatctc aataatga                                                        258
```

RECOMBINANT EXPRESSION VECTOR OF HUMAN PARATHYROID HORMONE

This application is a 371 of PCT/KR98/00146, filed Jun. 5, 1988.

This application claims priority under 35 U.S.C. §119 from Korean patent application Serial No. 1997/35230, filed Jul. 25, 1997.

BACKGROUND OF THE INVENTION

1. Field of the Invention

The present invention relates to a recombinant expression vector using phosphoribulokinase as a fusion partner and a process for preparing human parathyroid hormone therewith, more specifically, to a recombinant expression vector which is prepared by inserting a human parathyroid hormone gene containing an urokinase-specific cleavage site into a L-arabinose inducible vector containing a phosphoribulokinase gene fragment of *Rhodobacter sphaeroides* or its mutated gene- as a fusion partner, a recombinant microorganism transformed with the said expression vector, and a process for preparing human parathyroid hormone on a large scale by cultivating the said microorganism in a medium containing L-arabinose.

2. Description of the Prior Art

Osteoporosis is a disease causing harmful effects such as fracture even by small impact which results from reduction in mass of bone compared with normal people and weakness of bone tissue. The advance of medical science and biology leads to continuous increase in population of old age, which results in continuous increase of patients suffering from osteoporosis. Therefore, osteoporosis becomes a big social problem at present when number of old people living alone increases gradually according to a tendency of a nuclear family.

In general, in a normal bone tissue, balance between activities of osteoclast, a bone-destructing cell and osteoblast, a bone-forming cell is accomplished, which results in constant remodeling of bone tissue. In a normal body, osteoclast surpasses osteoblast in functioning according to increase in age, which results in overall decrease in bone density. In a patient suffering from osteoporosis, such a disruption in balance between activities of osteoclast and osteoblast is much higher than in normal case.

Although the cause of disruption in balance between activities of osteoclast and osteoblast has not been known clearly, it has been found that reduction in secretion of estrogen, a female hormone after the menopause causes osteoporosis type 1 which suffers women after the menopause largely. Thus, estrogen has been administered for the treatment of osteoporosis type 1, and many patients are, however, reluctant to use estrogen because of side effects such as high probability of attack of breast cancer, endometrium cancer, etc. Also, estrogen cannot be used for the treatment of osteoporosis type 2 which has been known to be induced by a cause different from that inducing osteoporosis type 1.

Calcitonin which inhibits activities of osteoclast to suppress resorption of bone tissue has been used as an agent which compensates for shortcomings of estrogen, an agent for the treatment of osteoporosis type 1 and treats osteoporosis type 2 not to be cured by estrogen. However, estrogen and calcitonin have no effect on increase in mass of bone which is already lost and only prevent further decrease in bone density. Therefore, they are improper for the effective treatment of osteoporosis.

Recently, parathyroid hormone (PTH) has been noticed as a good agent for the treatment of osteoporosis since PTH has an effect of increasing bone density as well as an effect of preventing reduction in bone density and its side effects have not been reported. Preproparathyroid hormone (preproPTH) which consists of 115 amino acids and is produced in main cells of parathyroid gland is processed and transformed into proPTH consisting of 92 amino acids while traveling through endoplasmic reticulum. Then, proPTH is further processed and transformed into mature PTH consisting of 84 amino acids while traveling through Golgi apparatus. PTH synthesized by the said processes is secreted into blood and transported to target organs, i.e., bone and kidney. Secreted PTH has a half-life of only 18 minutes.

PTH activates $Ca^{2+}$ pump in bone cell membrane to promote $CaHPO_4$ mobilization from bone which results in increase in blood $Ca^{2+}$ level within several minutes. Moreover, when PTH is secreted continuously, it activates osteoclasts already existed, stimulates formation of new osteoclasts, and inhibits activities of osteoblasts temporarily, which results in inhibition of $Ca^{2+}$ deposition into bone and stimulation of $Ca^{2+}$ release to increase secretion of $Ca^{2+}$ and $PO_4^{3-}$ into blood. On the other hand, secretion of PTH is regulated by blood $Ca^{2+}$ concentration through strong feedback mechanism. That is, 10% reduction-of blood $Ca^{2+}$ concentration in a short time doubles secretion of PTH. When blood $Ca^{2+}$ concentration is low for a long time, even 1% reduction of blood $Ca^{2+}$. concentration doubles secretion of PTH.

Unlike such a regulatory function of PTH in a living body, it has been reported that PTH stimulates formation of bone when external PTH is administered in a small dose intermittently (see: Tam, C. S. et al., Endocrinology, 110:506–512(1982)). The use of PTH for the treatment of osteoporosis is based on the said stimulatory function of PTH in formation of bone. Although the mechanism of stimulatory function of PTH in formation of bone has not been clearly understood, hypotheses such as inhibition of PTH secretion by the administered PTH, direct stimulation of osteoblasts and indirect stimulation of formation of bone through growth factor including insulin-like growth factor-1 (IGF-1) and transforming growth factor-β (TGF-β) have been suggested.

In order to treat osteoporosis by using PTH, administration of PTH for a long time is essentially required. However, processes for mass production of PTH have not been established so far, and practical application of PTH for the treatment of osteoporosis has been in a difficult situation. Thus, the present inventors have studied mass production of PTH from a recombinant microorganism employing genetic engineering technology and made an effort to remove amino-terminal methionine residue during expression of PTH in *E. coli* since Ser-Val-Ser amino acid sequence at amino-terminus of PTH has been reported to be essential for biological activity of PTH.

Methionine-specific amino peptidase, an enzyme removing translation-initiating methionine at amino-terminus of expressed proteins exists in *E. coli* which is widely used as a host cell for expression of a recombinant protein. However, when foreign proteins are expressed in large quantities in *E. coli*, removal of amino-terminal methionine is not achieved occasionally. Such a phenomenon has to be solved to construct an expression system of a protein whose amino acid sequence at amino-terminus affects its own biological activity, e.g., PTH.

In order to solve the said problem, three methods may be used mainly as followings: First, a desired protein is secreted into periplasm of *E. coli* or cultured medium in an amino-terminus processed form by expressing the desired protein in a fused form with secretion signal sequence at amino-terminus. The said method has an advantage that a mature protein is obtained by intracellular activity, while it has a shortcoming that yield of expression is relatively low. Secondly, after only a desired protein is expressed in *E. coli* and isolated from *E. coli* in a methionine-attached form at amino-terminus, it is digested with amino peptidase to obtain a mature protein. The said method has a shortcoming that purification of the protein is complex since separation of amino-terminal methionine-removed proteins from methionine-attached proteins is difficult. Thirdly, after a fusion protein where a desired protein is fused with another protein is expressed in *E. coli* and isolated, the fused partner is removed from the fusion protein employing an enzyme or a chemical agent to obtain a mature desired protein. The said method has an advantage of high efficiency of expression of a desired protein as well as production of an amino-terminal methionine-free protein.

On the other hand, methods for obtaining a desired protein from a fusion protein are largely classified into cleaving methods employing chemicals and enzymes. Among them, the cleaving methods employing chemicals have an advantage of low cost because of an use of chemicals of low-price. However, they have a shortcoming that an additional step for purifying a desired protein from byproducts is required since use of chemicals gives rise to produce various byproducts as well as a desired protein due to low specificity of chemicals to a cleaved site. On the contrary, the problem of the cleaving methods employing chemicals can be solved by the usage of enzymes due to their high specificity to a cleaved site. However, the cleaving methods employing enzymes have difficulties in practical application on industrial scale since price of enzymes is high.

In this regard, studies on the economical use of enzymes cleaving a fusion protein have been carried out in the art. However, mass production of Factor Xa, thrombin, enterokinase, etc. which are enzymes used for the said purpose is rather limited. Thus, the cleaving methods employing enzymes have not been used widely on an industrial scale regardless of their various advantages. Accordingly, there are strong reasons for exploring a third enzyme which can be produced in large quantities economically to be used efficiently for the cleaving methods employing enzymes. Since mass production of urokinase (two chain urokinase type plasminogen activator), a serine protease used as a thrombus-dissolving agent have been already developed and active urokinase can be prepared in large quantities employing expression system of prokaryote such as *E. coli* (see: W. E. Holmes et al, Bio/Technology, 3:923–929 (1985)), urokinase can be produced and obtained in large quantities economically compared with other enzymes such as Factor Xa, etc. Naturally, urokinase has been proposed as a potential candidate for the economical cleavage of a fusion protein and isolation of a desired protein.

Under the circumstances, the present inventors have determined amino acid sequence of urokinase-specific cleavage site within a protein, and discovered that cleavage efficiency is high when an amino acid sequence of -X-Gly-Arg (wherein, X represents Pro, Thr, Ile, Phe or Leu), an urokinase-specific cleavage site is present between a desired protein and a fusion partner in a fusion protein. Also, they have discovered that the highest cleavage efficiency cab be obtained in the presence of -Thr-Gly-Arg among the sequences (see: Korean patent laid-open publication No. 97-6495).

SUMMARY OF THE INVENTION

The present inventors have made an effort to prepare amino-terminal methionine-free PTH from a recombinant *E. coli* in large quantities, and discovered that recombinant PTH having an activity of native human PTH can be prepared on a large scale, by a process which comprises the steps of: inserting a human PTH gene which contains a urokinase-specific cleavage site and uses universal codon of *E. coli* into a L-arabinose inducible vector containing a phosphoribulokinase ("PRK") gene fragment of *Rhodobacter sphaeroides* or its mutated gene as a fusion partner to construct an expression vector, transforming *E. coli* with the said expression vector, isolating a fusion protein from the said transformed cell, and cleaving the fusion protein with urokinase.

A primary object of the invention is, therefore, to provide a recombinant expression vector which is prepared by inserting a human PTH gene containing an urokinase-specific cleavage site into a L-arabinose inducible vector containing a PRK gene fragment or its mutated gene.

The other object of the invention is to provide a recombinant microorganism transformed with the said expression vector.

Another object of the invention is to provide a process for preparing human PTH on a large scale by cultivating the said microorganism in a medium containing L-arabinose.

BRIEF DESCRIPTION OF THE DRAWINGS

The above and the other objects and features of the present invention will become apparent from the following descriptions given in conjunction with the accompanying drawings, in which:

FIG. 2 shows nucleotide sequences (SEQ ID NO:1 (#1); SEQ ID NO:2 (#2); SEQ ID NO:3 (#3), SEQ ID NO:4 (#4); SEQ ID NO:5 (#5); SEQ ID NO:6 (#6); SEQ ID NO:7 (#7); SEQ ID NO:8 (#8); SEQ ID NO:9 (#9); SEQ ID NO:10 (#10); SEQ ID NO: 11 (#11); SEQ ID NO:12 (#12); SEQ ID NO:13 (#13); SEQ ID NO:14 (#14)) of oligomers to prepare a human PTH gene.

DETAILED DESCRIPTION OF THE INVENTION

Figure 1:
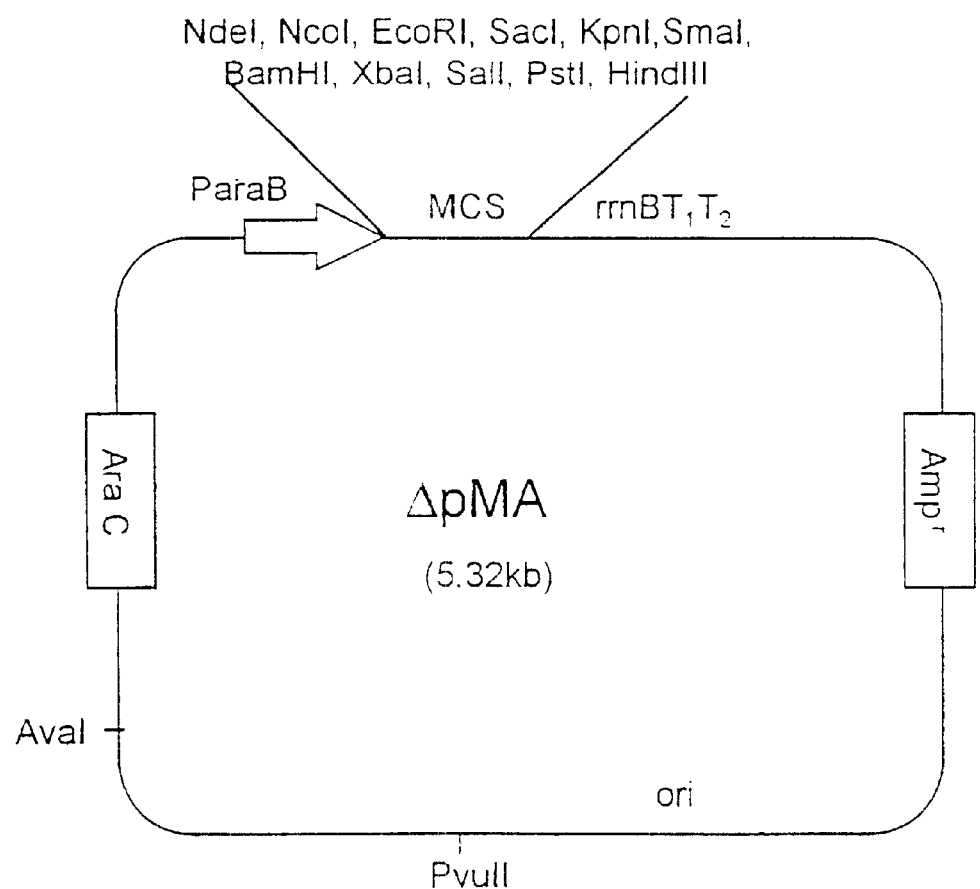
FIG. 1 shows a gene map of a ΔpMA expression vector.

A human PTH gene was first prepared to be translated into an amino acid sequence of native human PTH and to have a nucleotide sequence whose codons are frequently utilized in *E. coli*. Also, in order to obtain a desired protein from a fusion protein easily, an urokinase-specific cleavage site is synthesized and inserted before a human PTH gene so that an urokinase-specific cleavage site, i.e., an amino acid sequence of -X-Gly-Arg (wherein, X represents Pro, Thr, Ile, Phe or Leu), most preferably -Thr-Gly-Arg, is located between a desired protein and a fusion partner (see: Korean patent laid-open publication No. 97–6495).

And then, a p153PTH expression vector which contains the said urokinase-specific cleavage site-human PTH gene and a DNA fragment coding for 153 amino acids from amino-terminus of PRK was prepared. Then, the PRK gene fragment was isolated from the said expression vector, and part of the PRK amino acid sequence was modified and fused again with a human PTH gene to prepare an expression vector pm153PTH.

Since the said expression vectors used a PRK fragment coding for 153 amino acids from amino-terminus of PRK as a fusion partner, a lot of fusion proteins (human PTH fused with a PRK fragment) were expressed in microorganisms transformed with the said expression vectors. In this connection, *E. coli* transformed with pm153PTH expressed a fusion protein in the same or slightly increased quantities compared with *E. coli* transformed with p153PTH, which suggests that the amino acid substitution does not affect the expression of the fusion protein. On the other hand, employing an expression vector containing the said urokinase-specific cleavage site-human PTH gene and a full PRK gene also allowed expression of a fusion protein.

Moreover, as a result of cleaving the fusion protein consisting of a partially modified PRK fragment and human PTH and the fusion protein consisting of a native PRK fragment and human PTH with urokinase, respectively, it was found that the fusion protein consisting of a partially modified PRK fragment and human PTH shows reduction in nonspecific reaction by urokinase to obtain much more PTH under the same condition of the cleaving reaction using the same amount of the fusion protein.

The human PTH fused with PRK was expressed in a form of inclusion bodies in the transformants. After the inclusion bodies were isolated and treated with urokinase, recombinant human PTH was separated and purified from a PRK/PTH fusion protein.

On the other hand, it has been reported that PTH has an activity of regulating calcium stasis by promoting resorption of calcium from kidney and mineralized bone in a living body and increasing blood calcium concentration, and the said activity is mediated by cAMP (cyclic AMP), an intracellular secondary signaling molecule formed from ATP through binding of PTH to high-affinity receptors at surface of bone cell or renal cells which results in activation of adenylate cyclase associated with the receptor (see: Donahue, H. J. et al., Endocrinology, 126:1471–1477 (1990)). Grounded on the said knowledges, the present inventors determined binding affinity of PTH to the receptor present in bone cell or renal cell and level of stimulation of intracelluar cAMP formation in order to investigate whether the recombinant human PTH purified above has an activity of native PTH. As a result, it was found that the recombinant human PTH prepared above can bind the receptor and stimulate production of intracellular cAMP.

Accordingly, recombinant human PTH having an activity of native human PTH can be prepared in a high efficiency through the precise regulation of induction by cultivating a microorganism transformed with the recombinant expression vector of the invention, p153PTH or pm153PTH, and inducing expression of fusion protein by L-arabinose.

The present invention is further illustrated in the following examples, which should not be taken to limit the scope of the invention.

EXAMPLE 1

Construction of a ΔpMA Expression Vector

DNA was isolated from a *Salmonella typhymurium* LT2 strain, digested with EcoRI restriction enzyme, and inserted into a pUC19vector to prepare a pUC-Salmonella library. The pUC-Salmonella library was introduced to *E. coli* DH5α strain (*E. coli* DH5α F' endA1 hsdR17(rk⁻mk⁺) supE44 thi-1recA1 gyrA (Nair) U169D (lacZAY-argF) deoR) to obtain transformed *E. coli* colonies. On the other hand, two oligonucleotides complementary to the nucleotide sequence containing araB-C regulatory site in arabinose operon and 3 amino acids of araC protein from aminoterminus, i.e., 15mer of 5'-GCCATCGTCTTACTC-3' (SEQ ID NO:15) and 14mer of 5'-GCGTTTCAGCCATG-3' (SEQ ID NO:16) were synthesized. Colony hybridization using the oligonucleotides as probes was carried out to select a clone containing araB-A and araC genes from the pUC-Salmonella library prepared above.

The pUC-ara plasmid thus selected was digested with AvaI restriction enzyme, blunt-ended by Klenow enzyme and treated with SalI restriction enzyme to give a DNA fragment of 2.52 kbp. On the other hand, a pUC119 vector (see: Maniatis et al., Molecular Cloning 2nd ed., 1989) was digested with HindIII, blunt-ended by Klenow enzyme and treated with SalI to give a DNA fragment of 3.18 kbp. The two fragments thus obtained, i.e., the DNA fragment of 2.52 kbp and the DNA fragment of 3.18 kbp, were ligated by T4 DNA ligase to prepare a pUC-araBC vector of 5.7 kbp. After single stranded DNA was obtained from the vector thus obtained, a nucleotide sequence of NdeI restriction site, 5'-CATATG-3' (SEQ ID NO:17) was inserted into the translation initiation codon in a structural gene of araB protein located downstream of araB promoter, and site-specific mutation was carried out to transform a Shine-Dalgano nucleotide sequence in araB promoter into a sequence of 5'-TAAGGAGG-3' (SEQ ID NO:18).

The ara clone thus modified was digested with EcoRI and PvuII again to give a DNA fragment of 2.61 kbp containing an araB-C gene. On the other hand, a MpKL10 vector containing a multiple cloning site of 228 bp originated from pUC18 was digested with NdeI, blunt-ended by Klenow enzyme and ligated again by T4 DNA ligase to remove a NdeI restriction site in the said vector. The vector thus obtained was digested with EcoRI and PvuII to obtain a DNA fragment of 2.7 kbp containing a multiple cloning site, transcription termination signal, an ampicilin-resistance gene and a DNA replication origin of E. coli.

The DNA fragment of 2.61 kbp prepared above was ligated to the DNA fragment of 2.7 kbp prepared above, digested with NdeI and EcoRI, and ligated to a double stranded oligonucleotide which contains NcoI restriction site and has NdeI and EcoRI restriction sites at both ends, respectively, by T4 DNA ligase to construct a ΔpMA vector of about 5.32 kbp (see: Korean patent laid-open No. 97-5585). FIG. 1 shows a gene map of the ΔpMA thus constructed.

EXAMPLE 2

Preparation of a Human PTH Gene

In order to prepare a human PTH gene coding for native human PTH and having a nucleotide sequence whose codons are frequently utilized in E. coli, 12 oligonucleotides (SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14) corresponding to a sense and antisense strands of PTH were first synthesized (see: FIG. 2). The 12 oligomers were selectively ligated employing phosphorylation, annealing, elution and T4 DNA ligase. That is, in order to prevent self-ligation, ends of oligomers #2, #4, #5, #8, #9, #12 and #13 were phosphorylated and DNA annealing was carried out to produce pairs of #1:#2, #3:#4, #5:#6, #7:#8, #9:#10, #11:#12 and #13:#14. Then, after polyacrylamide gel electrophoresis, only oligomers of correctly annealed double strand, i.e., I, II, III, IV, V, VI and VII, were eluted. 3'-end of the double stranded oligomer VII has a cohesive end of XbaI restriction site, which allows easy cloning by using XbaI site of an expression vector.

Figure 3:
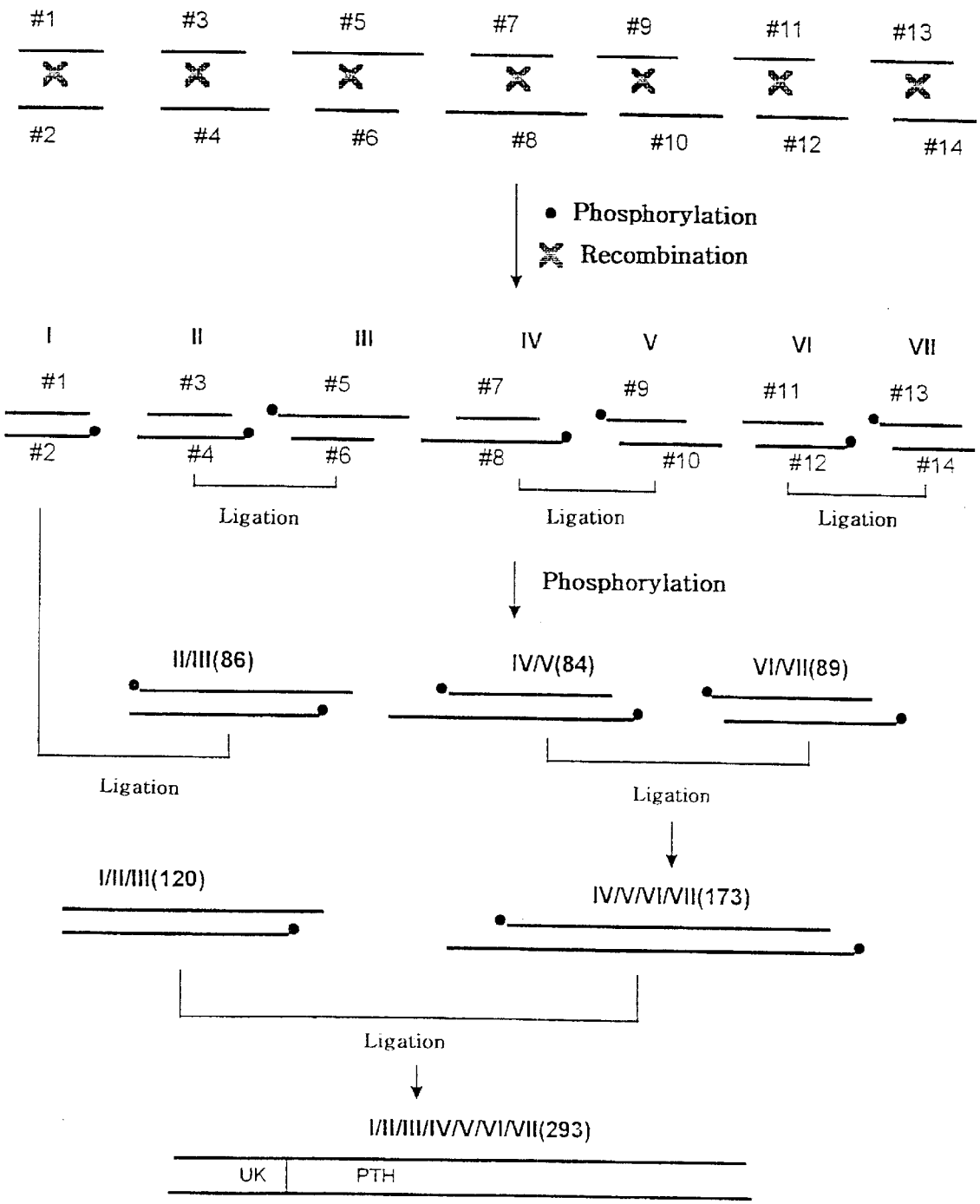
FIG. 3 is a schematic diagram showing ligation of the synthetic oligomers.

Ends of the double stranded oligomers thus eluted were phosphorylated, and II and III, IV and V, VI and VII were ligated by T4 DNA ligase, respectively. After polyacrylamide gel electrophoresis, correctly ligated DNA fragments of II/III, IV/V and VI/VII were eluted. Then, ends of the three fragments of II/III, IV/V and VI/VII were phosphorylated, and I and II/III, IV/V and VI/VII were ligated by T4 DNA ligase, respectively. And then, I/II/III and IV/V/VI/VII were ligated finally to synthesize a human PTH gene containing an urokinase-specific cleavage site and having a nucleotide sequence whose codons are frequently utilized in E. coli (see: FIG. 3). In FIG. 3, the number in a parenthesis indicates number of base. The double stranded oligomer 1 contains an urokinase-specific cleavage site whose synthesis is further illustrated in the following.

In order to separate PTH- easily from a fusion protein, an urokinase-specific cleavage site was synthesized and inserted between a fusion partner and a PTH gene as followings. The urokinase-specific cleavage site contained Gly-Thr-Gly-Arg (see: Korean patent laid-open publication No. 97-6495) and an amino acid of relatively low molecular weight was added before the said sequence to give flexibility. Also, 5'-end contained 3 restriction sites of SmaI, ScaI and PvuII to provide a blunt end so that any target gene can be fused in an easy manner considering its open reading frame. ABglII restriction site was located at the site linking the urokinase-specific cleavage site to a human PTH gene. Sense oligomer #1 and antisense oligomer #2 satisfying the said condition were synthesized and ligated. After polyacrylamide gel electrophoresis, correctly annealed double stranded oligomer I was eluted. Since both ends of double stranded oligomer I were blunt, only an oligomer #2 was phosphorylated before annealing to prevent formation of dimer and trimer of oligomer I. The double stranded oligomer I was ligated to be positioned ahead of the synthesized human PTH gene by T4 DNA ligase as mentioned above.

EXAMPLE 3

Construction of a PPRK Expression Vector Containing a PRK Gene

Chromosomal DNA was isolated from Rhodobacter sphaeroides strain and a PRK gene was amplified by performing polymerase chain reaction (PCR). In this connection, in order to subclone the PRK gene into the L-arabinose inducible expression vector (ΔpMA) prepared in Example 1 easily, translation initiation codon and a NdeI restriction site were introduced to a primer corresponding to the amino-terminal region of PRK which was used as 5' primer, and translation termination codon and a XbaI restriction site were introduced to a primer corresponding to the carboxy-terminal region of PRK which was used as 3' primer (5' primer: 5'-GGAGCTGAATACATATGAGCAAG-3' (SEQ ID NO:19); 3' primer: 5'-CCCCCGGGTCTAGATCAGGCCA-3' (SEQ ID NO:20).

Figure 4:
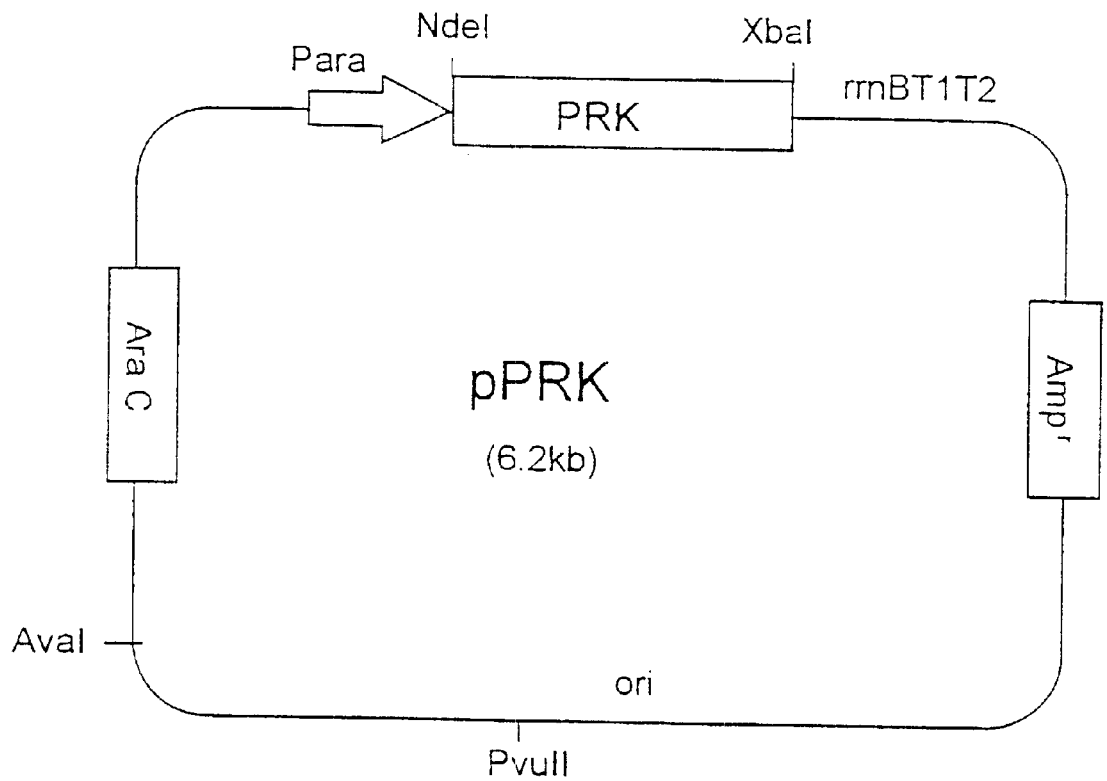
FIG. 4 shows a gene map of a pRK expression vector.

After 1% agarose gel electrophoresis of the PCR reaction product, a PRK gene of 873 bp was isolated, digested with NdeI and XbaI, and subcloned into a ΔpMA vector fragment treated with NdeI and XbaI to construct a pPRK expression vector (see: FIG. 4). E. coli MC1061(E. coli MC1061, F-araD139 Δ(ara-leu)7696 galE15 galK16Δ(lac) X74rpsL (Str$^r$) hsdR2 (rk$^-$mk$^+$) mcrA mcrB1) was transformed with the expression vector thus constructed and it was confirmed that a PRK protein having a molecular weight of 32 kDa was expressed from the transformant.

EXAMPLE 4

Fragmentation of the PRK Gene

Since use of the full PRK gene as a fusion partner has a shortcomging that yield of a finally desired protein is low due to a big fusion partner, size of PRK was reduced variously to decrease the size of a fusion partner for high yield of a desired protein. Since the structure of PRK has not been found yet, secondary structure of PRK protein was predicted by using a computer program (PROSIS, Hitachi, JAPAN) based on the method of Chou and Fasman (see: Adv. Enzymol., 47:45–148(1978); Annu. Rev. Biochem., 47:251–276(1978)). Then, two regions which was predicted not to form a secondary structure such as α-helix or β-strand (regions containing 113 and 153 amino acids from amino-terminus of PRK which were referred as to "113PRK" and "153PRK", respectively) were selected not to destroy structural stability of the protein.

Figure 5:
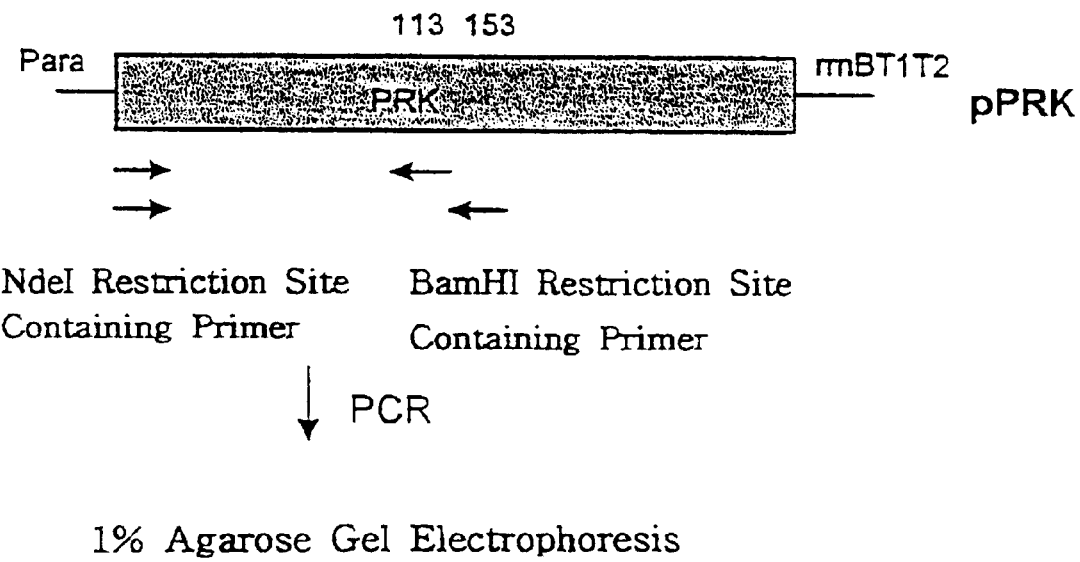
FIG. 5 shows a strategy to amplify the PRK gene fragment of the invention by PCR.

In order to amplify the PRK gene fragments, 5' primer in Example 3 was used as 5' primer, and oligonucleotides which correspond to nucleotide sequences containing 113th and 153th amino acids, respectively, and contain a BamHI restriction site for easy subcloning were used as 3' primer (3' primer for amplification of 113PRK: 5'-GGTGAAGGATCCGGGCGCCACGCCGGT-3' (SEQ ID NO :21); 5' primer for amplification of 153PRK: 5'-CGGAACGGATCCGATCTTGAGGTCGGC-3' (SEQ ID NO:22)) (see: FIG. 5).

The PRK gene fragments thus amplified were digested with NdeI and BamHI and isolated by performing 1% agarose gel electrophoresis.

The PCR products of 113PRK and 153PRK (gene fragments) thus isolated were digested with NdeI and BamHI, and inserted into ΔpMA digested with the same enzymes to construct p113PRK and p153PRK. *E. coli* MC1061(*E. coli* MC1061, F-araD139 Δ(ara-leu)7696 galE15 galK16Δ(lac) X74rpsL (Str$^r$) hsdR2(rk$^-$mk$^+$) mcrA mcrB1) was transformed with the said expression vectors, i.e., p113PRK and p153PRK, respectively, and cultured. As a result, it was found that 113PRK and 153PRK proteins were normally expressed in large quantities. Accordingly, it was confirmed that gene fragments coding for 113PRK and 153PRK proteins can be properly used as a fusion partner.

EXAMPLE 5

Construction of an Expression Vector p153PTH and Expression of PTH

Figure 6:
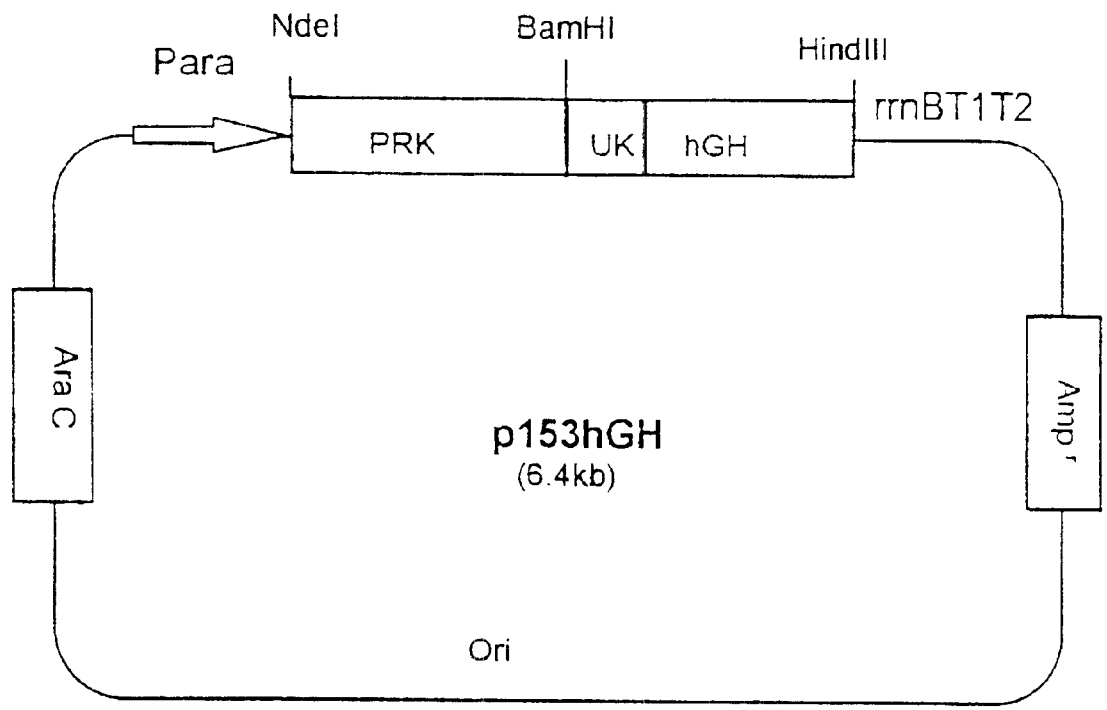
FIG. 6 shows a gene map of a p153hGH expression vector expressing a fusion protein of human growth hormone (hGH).

A pAI5UG expression vector of hGH which contains an urokinase-specific restriction site and a DNA fragment coding for 166 amino acids from amino terminus of IciA protein inhibiting replication initiation in *E. coli* as a fusion partner (see: Korean patent laid-open publication No. 97-6505) was digested with NdeI and BamHI to obtain a vector fragment containing a hGH gene and an urokinase (UK) restriction site of Thr-Gly-Arg. The 153PRK gene fragment isolated in Example 4 was subcloned into the vector thus obtained to construct an expression vector p153hGH (see: FIG. 6).

Figure 7:
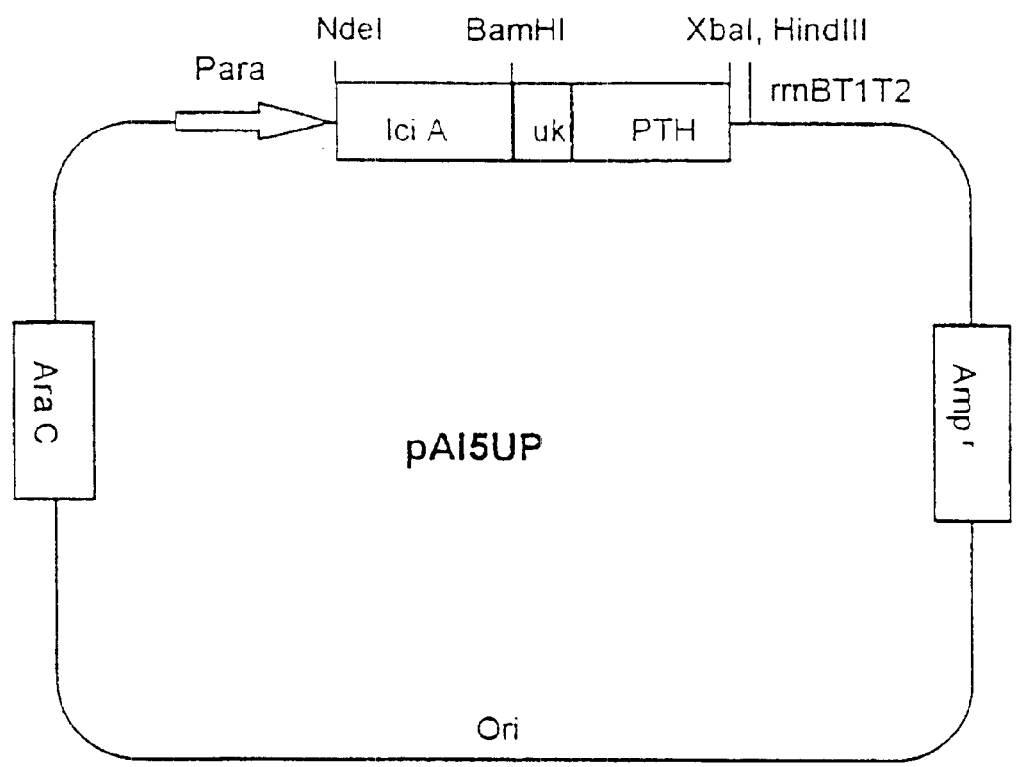
FIG. 7 shows a gene map of a pAI5UP expression vector expressing a fusion protein of PTH.

On the other hand, ΔpMA5S where a SmaI restriction site was inserted into a site of 166th amino acid codon from amino terminus of an IciA gene coding for the IciA protein inhibiting replication initiation in *E. coli* (see: Korean patent laid-open publication No. 97-6505, KCCM-10072) was digested with SmaI and XbaI to obtain a vector fragment containing an IciA gene fragment of 500 bp. The human PTH gene containing an urokinase-specific cleavage site which was synthesized in Example 2 was subcloned into the vector fragment thus obtained to construct a pAI-5UP vector which can express human PTH in a fused form with an IciA protein fragment containing 166 amino acids from amino terminus under the control of araB promoter system (see: FIG. 7, Korean patent laid-open publication No. 97-6497, KCCM-1007).

Figure 8:
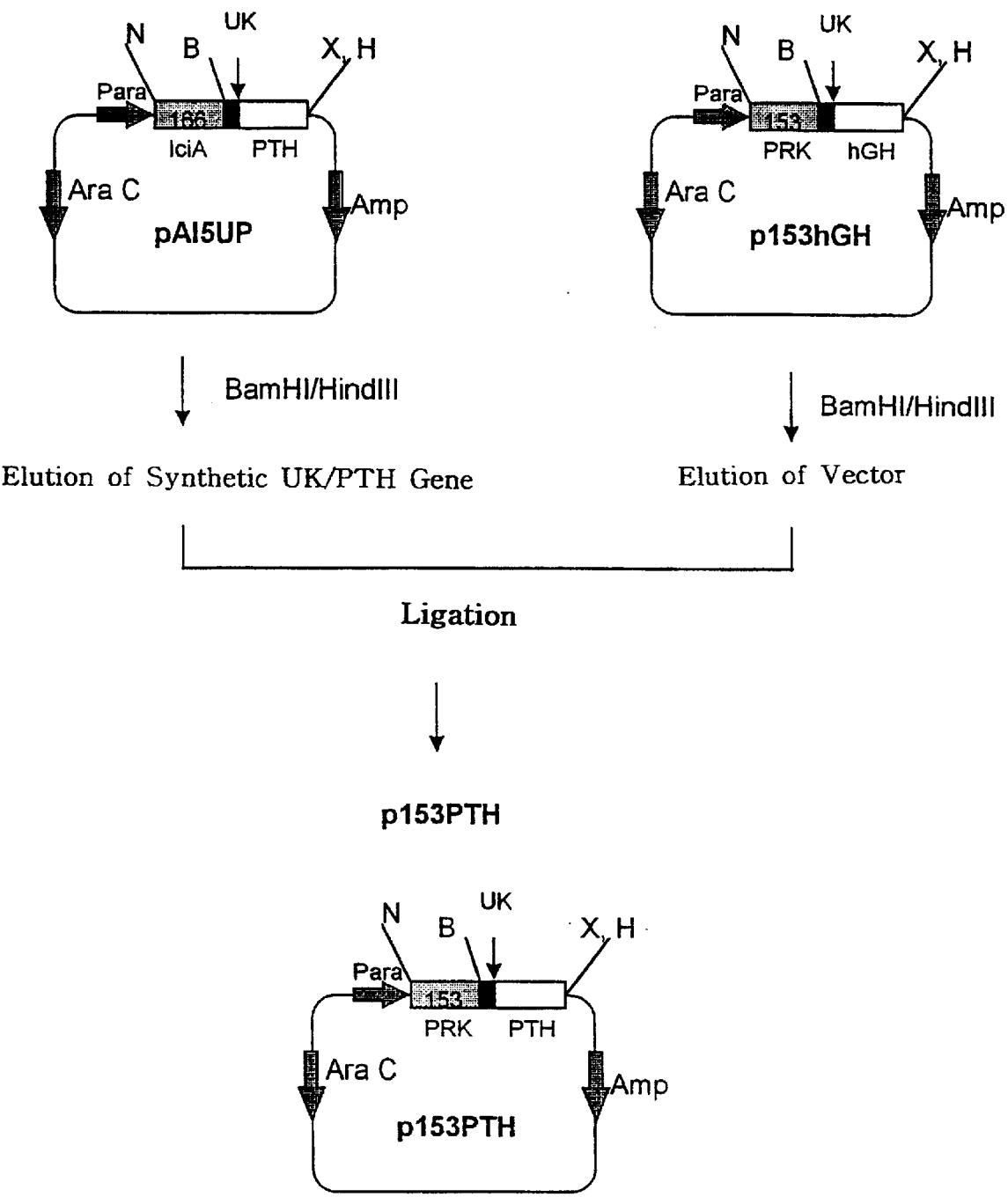
FIG. 8 shows a construction strategy to prepare a p153PTH expression vector of the invention which expresses recombinant human PTH.

The pAI5UP vector thus constructed was digested with BamHI and. HindIII to give a human PTH gene fragment containing an urokinase-specific cleavage site. The fragment thus obtained was subcloned into a vector fragment prepared by digesting p153hGH with BamHI and HindIII to construct a p153PTH vector which, under the control of araB promoter system, can express a human PTH fusion protein containing an urokinase-specific cleavage site and 153PRK (consisting of 153 amino acids from amino-terminus of PRK) as a fusion partner (see: FIG. 8).

*E. coli* MC1061 (F-araD139 Δ (ara-leu) 7696 galE15 galK16 D (lac)X74 rpsL (Str$^r$) hsdR2(rk$^-$mk$^+$) mcrA mcrB1) was transformed with the p153PTH expression vector thus constructed, and the resultant transformant was inoculated in a LB liquid medium containing ampicilin (containing 5 g of NaCl, 5 g of yeast extract, 10 g of bacto tryptone and 50 mg of ampicilin per 1 L of medium) and cultured at 180 rpm at 37° C. for 1 day. Confluent medium was inoculated again in a fresh LB liquid medium containing ampicilin to reach a final concentration of 1% and cultured under shaking until absorbance at 600 nm reached to 0.5. Then, L-arabinose was added to the cultured medium to reach a final concentration of 1% to induce expression of a 153PRK/PTH (hereinafter, referred to as "153PTH" for convenience) fusion protein and the cells were cultured under shaking for about 20 hours.

Figure 9:
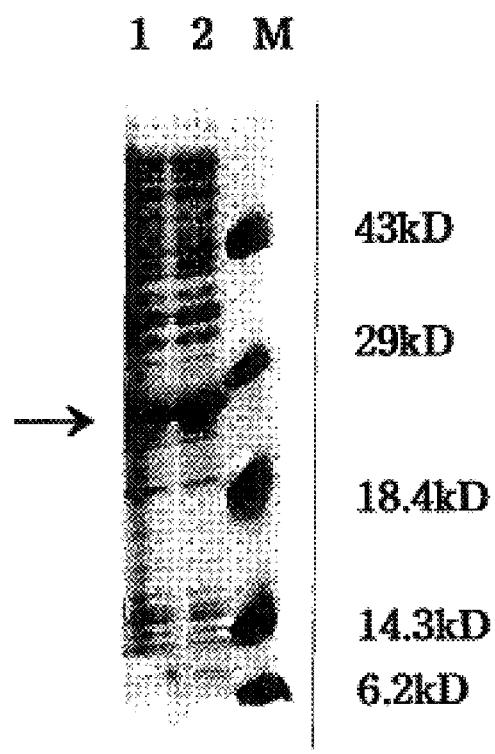
FIG. 9 is a photograph showing electrophoresis pattern which shows expression of human PTH protein fused with PRK fragment in *E. coli* transformed with pl53PTH during L-arabinose induction.

As a result of SDS-PAGE analysis of total proteins of cultured *E. coli* cells, it was found that a 153PTH fusion protein of about 26 kDa was expressed in *E. coli* in a high efficiency during L-arabinose induction (see: FIG. 9). In FIG. 9, lanes 1 and 2 show total proteins of *E. coli* MC1061 transformed with p153PTH which was cultured for 20 hours after 1% L-arabinose induction; and, lane M shows standard protein marker (BRL 16040-016, USA)

*Escherichia coli* MC1061 transformed with the p153PTH expression vector was designated as *Escherichia coli* MC1061:p153PTH, and deposited with the Korean Culture Center of Microorganisms (KCCM), an international depositary authority located at 134 Shinchon-Dong, Seodaemun-Ku, Seoul, Korea, under an accession No. KCCM-10101 on Jul. 9, 1997.

EXAMPLE 6

Isolation and Digestion of Inclusion Bodies of a 153PTH Fusion Protein

Figure 10:
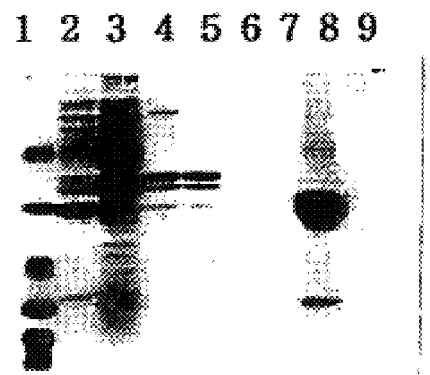
FIG. 10 is a photograph showing SDS-PAGE pattern of samples obtained during the isolation of a fusion protein expressed in *E. coli* transformed with p153PTH.

It was investigated whether 153PTH fusion proteins which were expressed in *E. coli* MC1061 transformed with the p153PTH (KCCM-10101) during L-arabinose induction as in Example 5 may form inclusion body. Cultured *E. coli* cells which were obtained after centrifugation were suspended in Tris buffer (50 mM Tris buffer (pH 7.8) containing 0.1 mM EDTA and 25% sucrose). Lysozyme was added to the cell suspension and incubated for 1.5 hours on ice. Then, MgCl$_2$ and DNaseI were added to the cells and incubated for 1.5 hours. And then, a buffer containing 1% deoxycholic acid and 1.6% Nonidet P-40 was added to the cells, and stirred for 15 minutes on ice. And, the cells were lysed by ultrasonication. The cell lysate was centrifuged to separate fraction of inclusion body from aqueous fraction, and the fraction of inclusion body was washed with 0.5% Triton X-100 solution four times. The inclusion bodies thus obtained were stirred in 8M urea solution at 4° C. slowly for denaturation. Aliquots sampled during the isolation of inclusion bodies were analyzed by SDS-PAGE (see: FIG. 10).

In FIG. 10, lanes 2, 3, 4 to 7 and 8 show cell lysate, supernatant of cell lysate, washed solutions of inclusion bodies and denaturated inclusion bodies, respectively; lane shows standard protein size-marker of BRL 16040-016 such as 43 kD, 29 kD, 18.4 kD, 14.3 kD, 6.2 kD and 3.4 kD according to molecular weight; and, lane 9 shows standard protein marker of NEB 7707L such as 175 kD, 83 kD, 62 kD, 47.5 kD, 32.5 kD, 25 kD, 16.5 kD and 6.5 kD according to molecular weight. As shown in FIG. 10, it was revealed that a 153PTH fusion protein was expressed in *E. coli* in large quantities and can be isolated in a form of inclusion body.

After quantitation of the isolated 153PTH fusion protein was carried out, 0.5 μg of urokinase was added to 100 μg of the 153PTH fusion protein and reacted at 25° C. for 1 hour.

Figure 11:
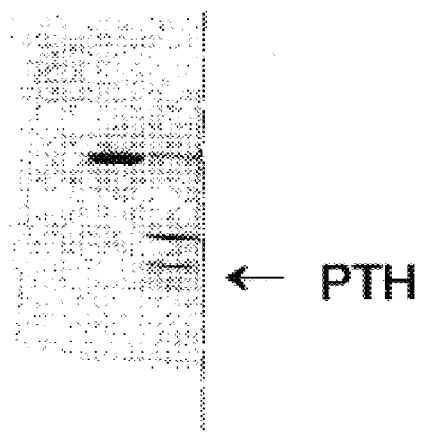
FIG. 11 is a photograph showing SDS-PAGE pattern of inclusion bodies of 153PTH fusion protein after urokinase digestion.

Then, level of cleavage was investigaed by SDS-PAGE (see:

FIG. 11). In FIG. 11, lane 1 shows the 153PTH fusion protein without addition of urokinase as a control; lane 2 shows the 153PTH fusion protein with addition of urokinase; and, lane M shows standard protein size-marker (NEB7707L, 175 kD, 83 kD, 62 kD, 47.5 kD, 32.5 kD, 25 kD, 16.5 kD and 6.5 kD according to molecular weight). When the 153PTH fusion protein is cleaved by urokinase, a fusion partner of a molecular weight corresponding to 153 amino acids and a desired PTH protein of a molecular weight corresponding to 84 amino acids have to be produced. As shown in FIG. 11, it was found that a PTH protein of about 10 kD appeared according to expectation. However, it was revealed that an expectative 153PRK protein fragment of about 17 kD, i.e., a fusion partner, did not almost appear and various protein fragments of smaller size appeared. Therefore, it was suggested that nonspecific cleavage by urokinase occurred at some of 12 arginine residues of 153PRK.

EXAMPLE 7

Construction of an Expression Vector pm153PTH and Expression Therewith

In order to reduce additional cleavage of 153PRK by urokinase, arginine residues locating at possible sites of additional cleavage were removed. Considering size of protein fragments produced during cleavage of 153PTH by urokinase, it was expected that additional cleavage can occur at 30th, 31th, 58th, 59th, 94th and 96th arginine residues from amino-terminus of PRK. Thus, the present inventors attempted to substitute those arginine residues with other amino acids.

Figure 12:
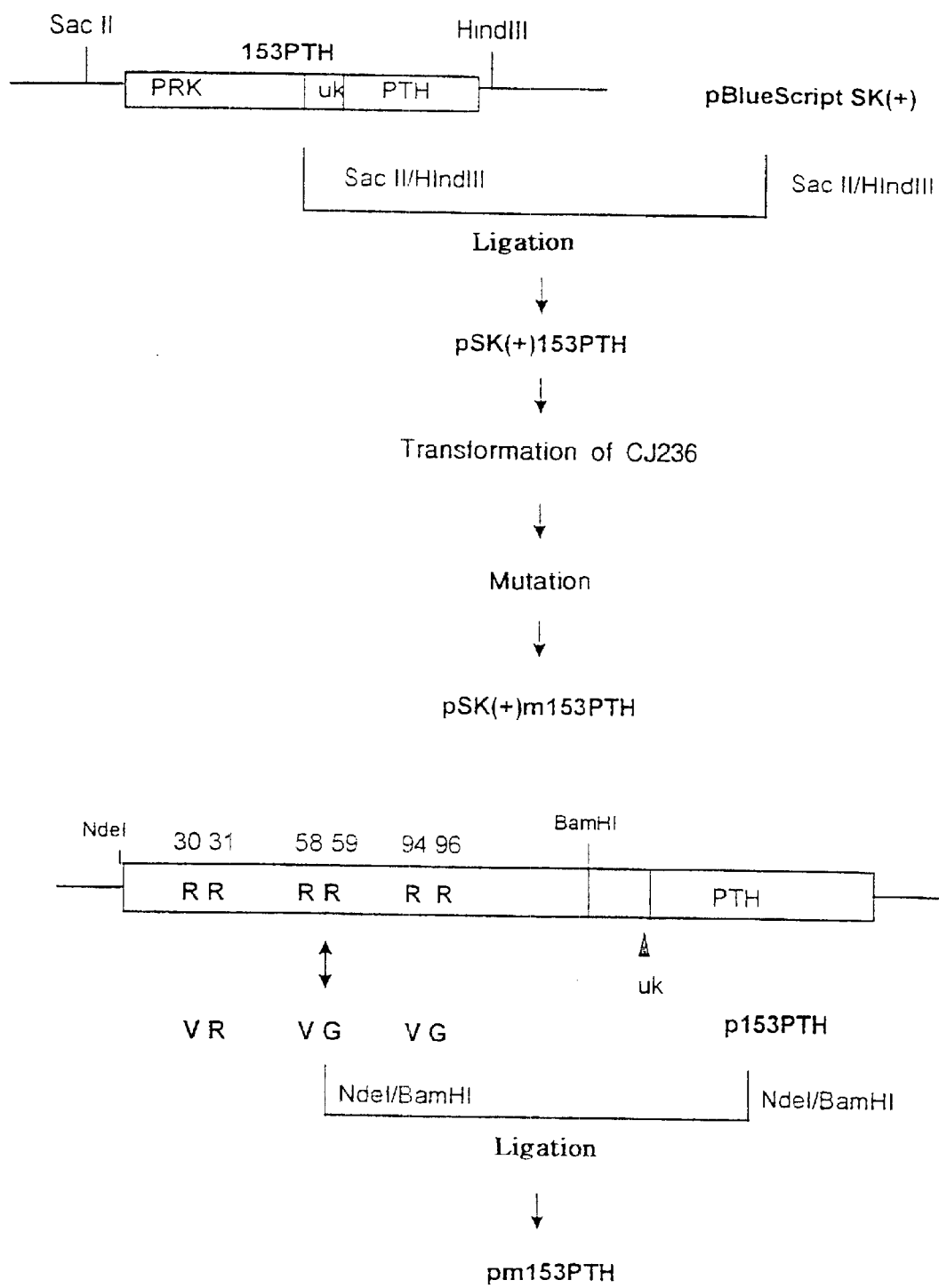
FIG. 12 shows a construction strategy to prepare a pm153PTH expression vector of human PTH of the invention by modifying p153PTH.

That is, a 153PTH gene fragment which was isolated after digestion of an expression vector p153PTH with SacII and HindIII was inserted into a vector fragment which was prepared by digesting pBlueScript SK (+) (Stratagene, USA) with SacII and HindIII to give a plasmid for mutation, pSK (+) 153PTH by which single stranded DNA was obtained (see: FIG. 12). E. coli CJ236 was transformed with pSK (+)153PTH, and site-specific mutation was performed according to Kunkel et al. 's method (see: Kunkel, T. A., Proc. Natl. Acad. Sci., USA, 82:488–492(1985)). In this connection, mutamers were used as followings:

30/31 mutamer:
5'-CCTTGACCCCCTCGC                (C/G)
CACGAAGATCTGGTCGAAC-3' (SEQ ID NO:23);
58/59 mutamer:
5'-GCCCGCCGCATAGC                 (G/C)
CACGTCCAGCTCGGCCTTC-3' (SEQ ID NO:24);
94/96 mutamer:
5'-GACGTAGGTCC                    (C/G)
CGTCACCCCCTGCCCGGTCTCGCC-3' (SEQ ID NO:25)

A mutant vector where 30th, 58th and 94th arginines were substituted with valines and 59th and 96th arginines were substituted with glycines was prepared by using the mutamers and named as pSK(+)m153PTH. A mutated 153PRK fragment obtained by digesting pSK(+)m153PTH with NdeI/BamHI and a vector fragment containing urokinase/PTH which was prepared by digesting an expression vector p153PTH with NdeI/BamHI were ligated by T4 ligase to construct an expression vector pm153PTH (see: FIG. 12).

Figure 13:
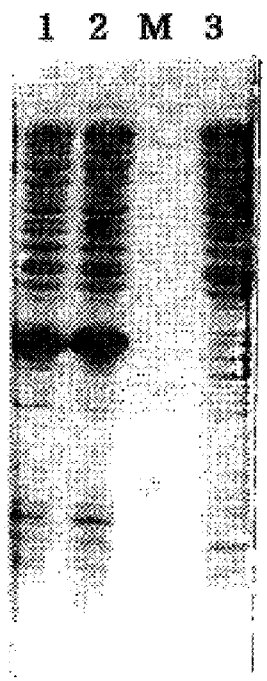
FIG. 13 is a photograph showing electrophoresis pattern which shows expression of a fusion protein in *E. coli* transformed with pm153PTH during L-arabinose induction.

E. coli MC1061(F-araD139 Δ(ara-leu)7696 galE15 galK16 D(lac)X74 rpsL (Str$^r$) hsdR2(rk$^-$mk$^+$) mcrA mcrB1) was transformed with the pm153PTH expression vector and cultured in the same manner as in Example 5. SDS-PAGE analysis revealed that a m153PRK/PTH (hereinafter, referred to as "m153PTH") fusion protein was expressed (see: FIG. 13). In FIG. 13, lane 1 shows total proteins of E. coli MC1061 transformed with an expression vector p153PTH which was cultured for 20 hours after 1% arabinose induction; lane 2 shows total proteins of E. coli MC1061 transformed with an expression vector pm153PTH which was cultured for 20 hours after 1% arabinose induction; lane 3 shows total proteins of E. coli MC1061 transformed with an expression vector pm153PTH before 1% arabinose induction; and, lane M shows standard protein size-marker (NEB7707L, 83 kD, 62 kD, 47.5 kD, 32.5 kD, 25 kD, 16.5 kD and 6.5 kD according to molecular weight) As shown in FIG. 13, it was found that E. coli transformed with pm153PTH expressed a fusion protein in the same or slightly increased quantities compared with E. coli transformed with p153PTH, which shows no reduction of expression by amino acid substitution.

Escherichia coli MC1061 transformed with the pm153PTH expression vector was designated as Escherichia coli MC1061:pm153PTH, and deposited with the Korean Culture Center of Microorganisms (KCCM), an international depositary authority located at 134 Shinchon-Dong, Seodaemun-Ku, Seoul, Korea, under an accession No. KCCM-10102 on Jul. 9, 1997.

EXAMPLE 8

Isolation and Digestion of Inclusion Bodies of a m153PTH Fusion Protein

Figure 14:
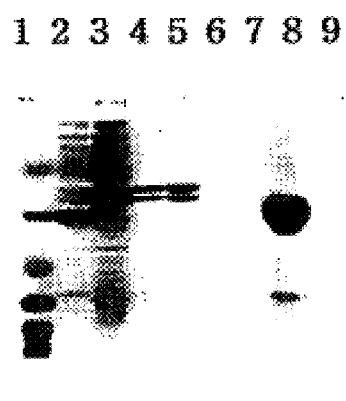
FIG. 14 is a photograph showing SDS-PAGE pattern of samples obtained during the isolation of a fusion protein expressed in *E. coli* transformed with pm153PTH.

In order to investigate how the m153PTH fusion protein is expressed in E. coli, aliquots sampled during the isolation of inclusion bodies were analyzed by SDS-PAGE in the same manner as in Example 6 (see: FIG. 14). In FIG. 14, lanes 2, 3, 4 to 7 and 8 show cell lysate, supernatant of cell lysate, washed solutions of inclusion bodies and denaturated inclusion bodies, respectively; lane 1 shows standard protein size-marker of BRL 16040-016 such as 43 kD, 29 kD, 18.4 kD, 14.3 kD, 6.2 kD and 3.4 kD according to molecular weight; and, 1 and 9 shows standard protein size-marker of NEB 7707L such as 175 kD, 83 kD, 62 kD, 47.5 kD, 32.5 kD, 25 kD, 16.5 kD and 6.5 kD according to molecular weight. As shown in FIG. 14, it was revealed that, like a m153 fusion protein, a m153PTH fusion protein formed inclusion body within a cell.

Figure 15:
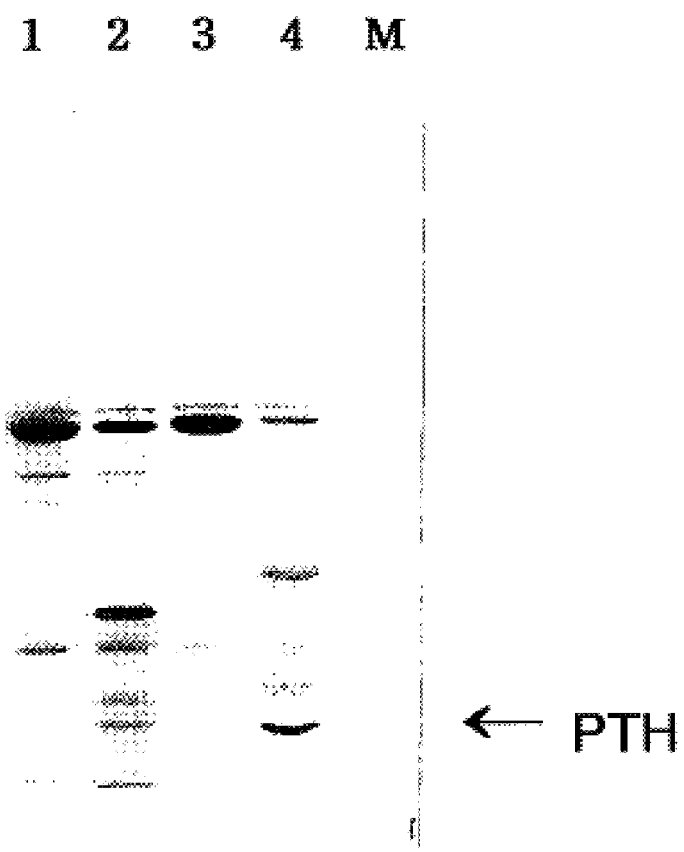
FIG. 15 is a photograph showing SDS-PAGE pattern of inclusion bodies of 153PTH and m153PTH fusion proteins after urokinase digestion.

After quantitation of the isolated fusion protein was carried out in the same manner as in Example 6, 0.5 μg of urokinase was added to 100 μg of the 153PTH or m153PTH fusion protein and reacted at 25° C. for 1 hour. Then, level of cleavage was investigaed by SDS-PAGE (see: FIG. 15). In FIG. 15, odd lanes show a fusion protein without addition of urokinase as a control and even lanes show a fusion protein with addition of urokinase; lanes 1 and 2 show a 153PTH fusion protein; lanes 3 and 4 show a m153PTH fusion protein; and, lane M shows standard protein size-marker (NEB7707L, 175 kD, 83 kD, 62 kD, 47.5 kD, 32.5 kD, 25 kD, 16.5 kD and 6.5 kD according to molecular weight). As shown in FIG. 15, it was found that nonspecific cleavage by urokinase decreased in cleavage of a m153PTH fusion protein compared with that of 153PTH fusion protein. Accordingly, more PTH can be obtained from m153PTH fusion proteins than 153PTH fusion proteins, under the same reaction condition as well as the use of the same quantity of the fusion protein.

Figure 16:
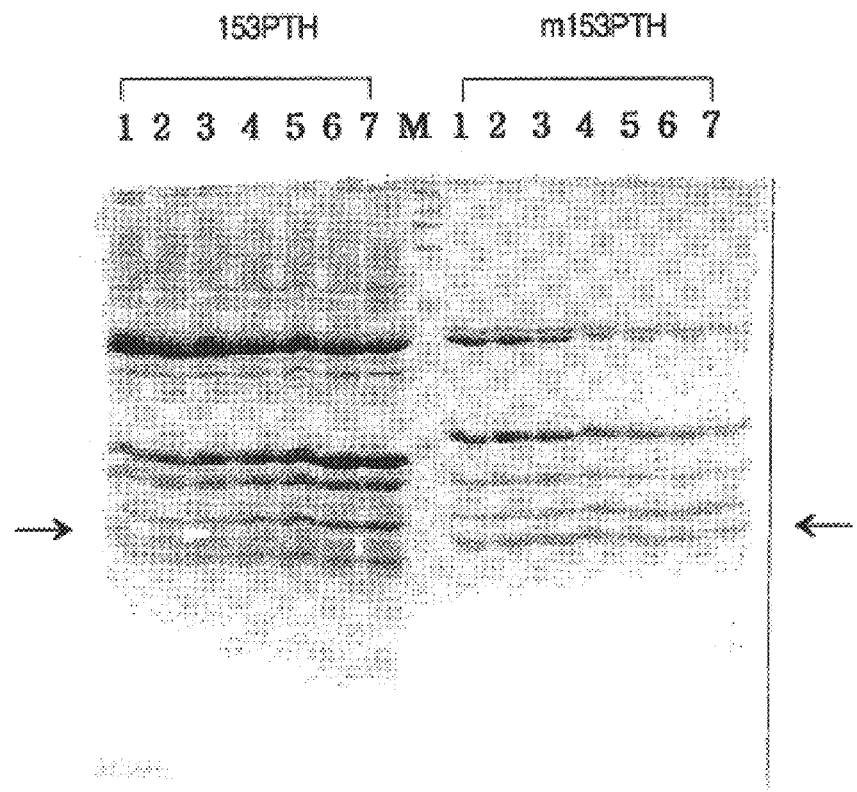
FIG. 16 is a photograph showing electrophoresis pattern of various reactants to compare efficiency of urokinase digestion of inclusion bodies of 153PTH and m153PTH.

Moreover, in order to compare cleavage efficiency of 153PTH and m153PTH fusion proteins by urokinase according to cleavage time, the fusion protein and urokinase were mixed in a concentration ratio of 200:1 and reacted at 25° C. for cleavage. Then, aliquots were collected according to time and analyzed by SDS-PAGE (see: FIG. 16). In FIG. 16, lanes 1 to 7 show samples digested with urokinase for 20, 30, 60, 150, 190, 225 and 360 minutes, respectively.

As shown in FIG. 16, it was revealed that the m153PTH. fusion protein was cleaved almost completely after the reaction for 60 minutes and the m153PTH fusion protein was not cleaved completely even after the reaction for 6 hours.

From the said comparative experiment of cleavage, it was found that the m153PTH fusion protein shows increased yield of PTH obtained per time and per urokinase used, compared with the 153PTH fusion protein.

EXAMPLE 9

Purification of Recombinant Human PTH

Figure 17:
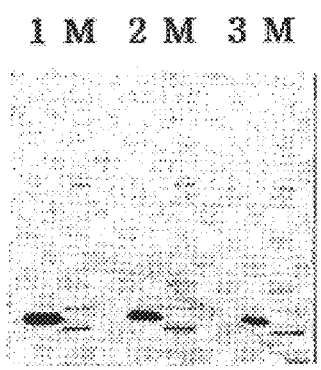
FIG. 17 is a photograph showing SDS-PAGE pattern of purified human PTH.

Quantitation of the m153PTH fusion protein in inclusion bodies isolated in the same manner as in Example 8 was carried. out and the protein was diluted with Tris buffer to reach a protein concentration of 1 mg/ml. Urokinase (protease) was added to the solution and reacted at 25° C. to separate PTH from the fusion proteins. The separated PTH proteins were purified by using ion-exchange resin and $C_{18}$ reverse HPLC chromatography and analyzed by SDS-PAGE (4–20% gradient gel), which was shown in FIG. 17. In FIG. 17, lanes 1 to 3 show 15, 7.5 and 3.75 µg of the purified PTH, respectively; and, lane M shows molecular weight marker of standard protein (Novex LC 5677, 200 kD, 116.3 kD, 97.4 kD, 66.3 kD, 55.4 kD, 36.5 kD, 31 kD, 21.5 kD, 14.4 kD, 6 kD and 3.5 kD according to molecular weight) . As shown in FIG. 17, it was revealed that a human recombinant PTH was purified in an isolated form.

EXAMPLE 10

Determination of Activity of the Human Recombinant PTH

UMR106 cell line (rat osteoblast-like osteosarcoma cell line) has been widely used for studies on characterisitcs of osteoblast and it has been known that the cell line shows high activity of alkaline phosphatase, i.e., one of characterisitcs of osteoblast, and produces type I collagen (see: Meika A. Fang et al., Endocrinology, 131(5) :2113–2119 (1992); Cheryl O. Quinn et al., The Journal of Biological Chemistry, 265(36) :22342–22347(1990) ). Thus, in vivo activity of the human recombinant PTH (rhPTH (1–84)) purified in Example 9 was determined by a binding test to PTH receptor and a stimulating test of intracellular cAMP production using UMR 106 cell line (ATCC CRL 1661). In this connection, synthetic human PTH (shPTH (1–84), Sigma Chemical Co., USA) was used as a control and quantitation of PTH was carried out by using "Allegro Intact PTH RIA kit (Nichols Institute,. San Juan Capistrano, USA)" which detects only intact PTH having amino- and carboxy-terminus (see: Samuel R. Nussbaum et al., Clinical Chemistry, 33(8):1364–1367(1987)). On the other hand, UMR106 cell line was cultured in DMEM (Dulbecco's Modified Eagle Medium) containing 0.2% sodium bicarbonate and 10% FBS (fetal bovine serum, heat-treated at 56° C. for 30 minutes) at 37° C. under an environment of 5% $CO_2$ (see: Ronald J. Miduraet al., The Journal of Biological Chemistry, 269(18):13200–13206(1994)).

EXAMPLE 10-1

A Binding Test to PTH Receptor

A binding test to PTH receptor was carried out as followings (see: Chohei Shigeno et al., The Journal of Biological Chemistry, 263(8):3864–3871(1988)): $10^5$ UMR106 cells per well was added into a 24 well-plate and cultured for 4 to 8 days. Medium was exchanged every two days and it was exchanged daily at 3 days before the test. On the other hand, in order to prepare ($Nle^{8,18}Tyr^{34}$)-bovine PTH (1–34)-$NH_2$(bPTH (1–34)) (see: Gino V. Segre et al., JBC, 254(15) :6980–6986(1979)) which was labelled with a radioactive isotope, $^{125}I$ at a tyrosine residue of carboxy-terminus, bPTH (1–34) was iodinated with $Na^{125}I$ using chloramine T (Sigma Chemical Co., USA) as a catalyst. The iodination products was loaded onto a $C_{18}$ Sep-Pak column and iodinated bPTH was eluted with 50% ACN (acetonitrile)/0.1% TFA (trifluoroacetic acid) to remove free $^{125}I$. Then, ACN was removed from the isolated bPTH.

Binding affinity of PTH to its receptor was determined by comparing competitive inhibition of rhPTH (1–84) and shPTH (1–84) against ligand binding to the receptor by using the $^{125}I$-labelled ($Nle^{8,18}Tyr^{34}$)-bPTH (1–34) as a ligand. Ligands and the said PTHs were diluted with binding buffer (50 mM Tris buffer (pH 7.7) containing 100 mM NaCl, 5 mM KCl, 2 mM $CaCl_2$, 5% horse serum and 0.5% FBS), respectively. On the other hand, the 24 well-plate obtained after culture as above was cooled on ice, washed with 1 ml of the binding buffer twice, and added with ligand of 30000 to 50000 cpm and competitive PTH of various concentration to reach a final volume of 0.3 ml. Each diluent of hormone was added to 3 wells concurrently and adsorbed at 15° C. for 4 hours. After the reaction, the wells were washed with 0.5 ml of the binding buffer four times to remove free radioactive isotopes. Then, 0.5 ml of 0.5M NaOH was added, and radioactive isotopes binding to the cells were extracted at room temperature for 16 to 18 hours. The solution obtained after extraction was mixed with the solution obtained after washing with 0.5 ml of the binding buffer and counted for its radioactivity employing γ-counter.

Figure 18A:
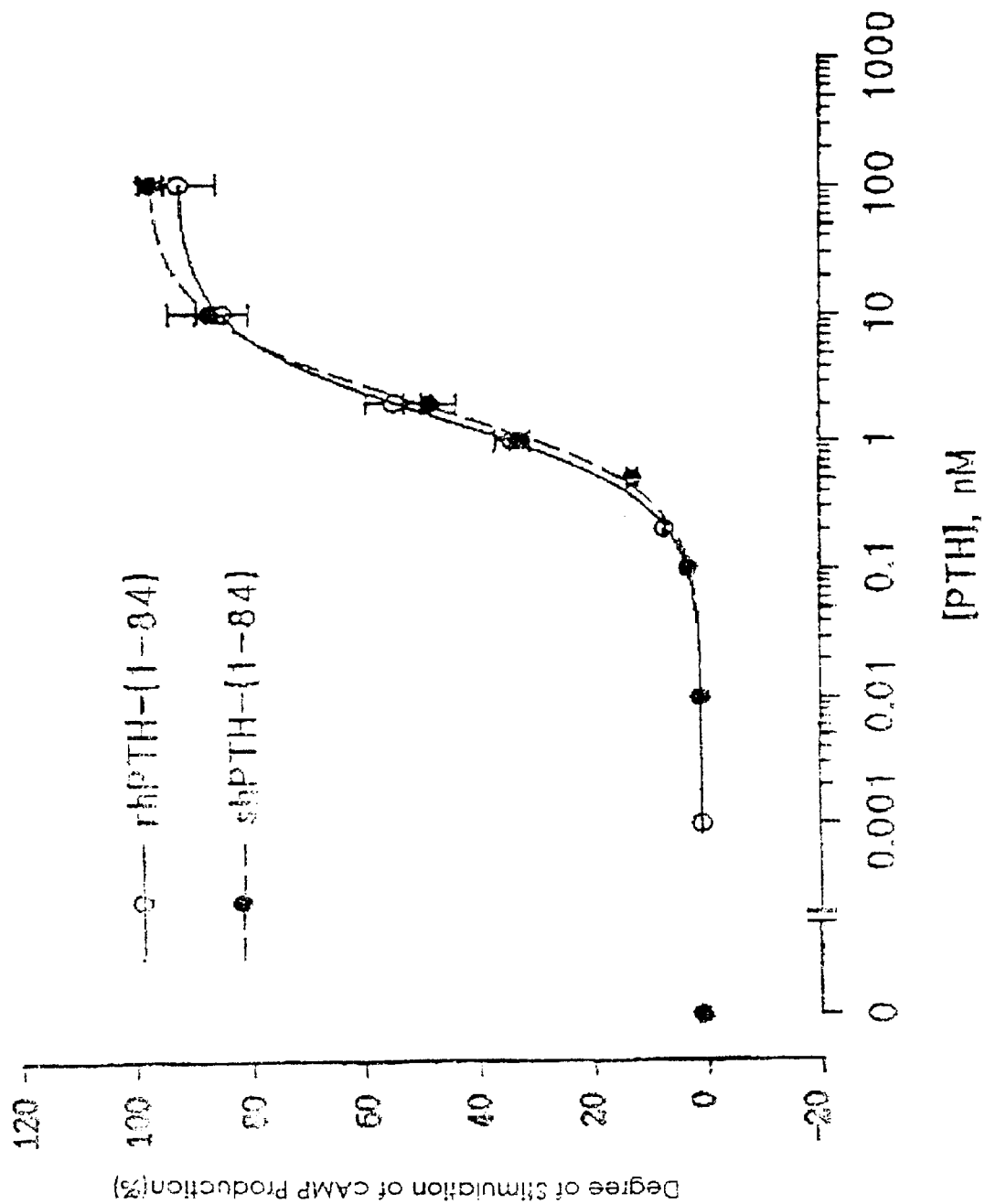
FIG. 18(A) is a graph showing that purified human PTH stimulates production of intracellular cAMP.

Specific binding was determined by subtracting value of nonspecific binding measured by using each competitive hormone of 1 mM from value of binding radioactivity measured above. Determined value was expressed as a percentage against maximum specific binding, and optimization of curve and $IC_{50}$ (50% inhibitory concentration: concentration of hormone required for reducing binding of ligand in 50%) which is an important index for comparison of binding affinity of each competitive hormone were determined according to fig.P program of Biosoft Co. $IC_{50}$ values of shPTH (1–84) and rhPTH (1–84) were 18.6±1.5 and 17.3±3.1 nM (the average value±the standard deviation), respectively. One of the results was shown in FIG. 18(A). As shown in FIG. 18(A), it was found that the recombinant PTH had the same binding activity to the receptor as the synthetic PTH.

EXAMPLE 10-2

A Stimulating Test of Intracellular cAMP Production

Figure 18B:
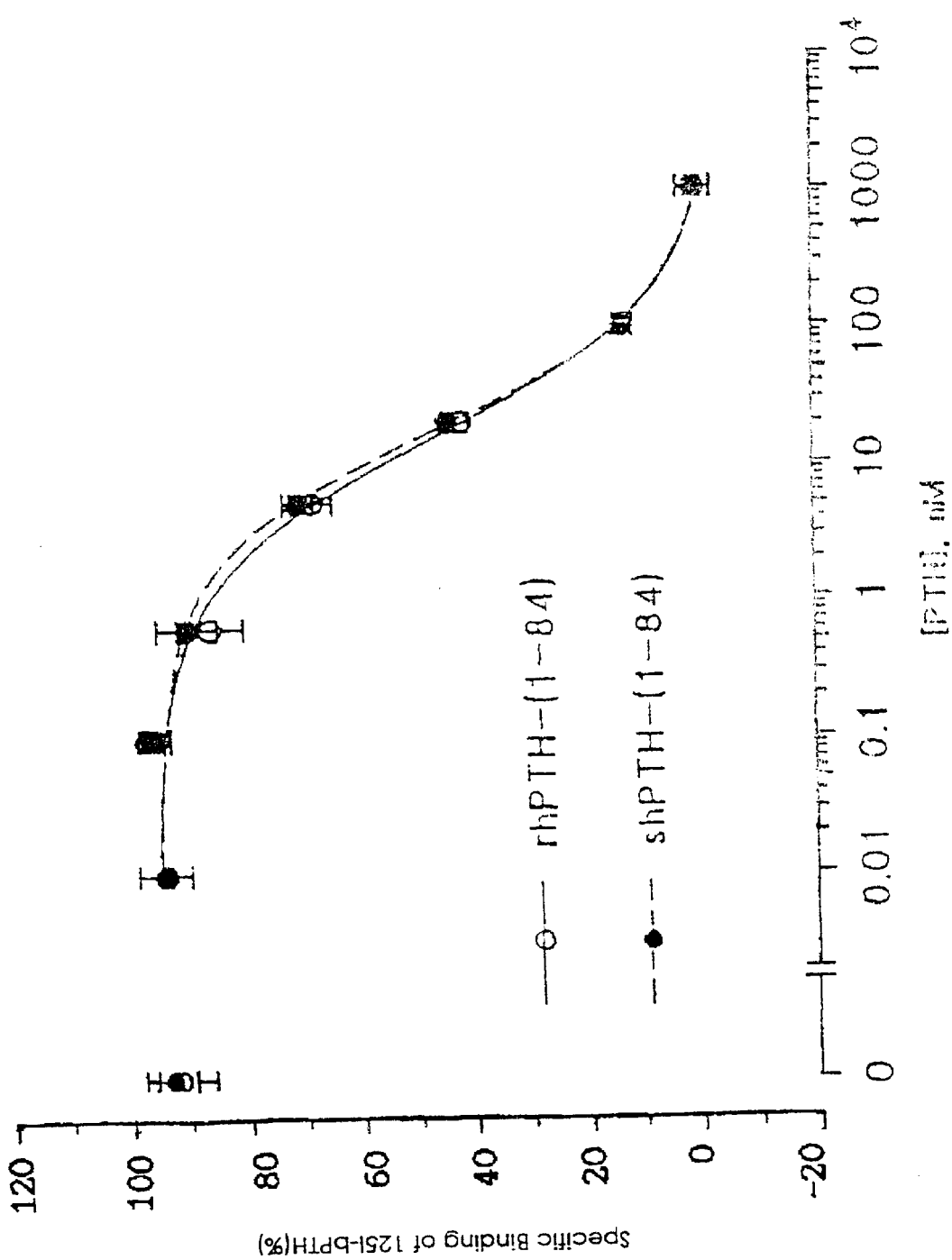
FIG. 18(B) is a graph which shows binding of purified human PTH to its receptor.

A stimulating test of intracellular cAMP production was carried out as followings (see: Thomas J. Gardella et al., JBC, 265(26):15854–15859(1990)): The UMR cells cultured in a 24 well-plate for 4 to 8 days in Example 10-1 were cooled for 15 minutes on ice and washed with 0.25 ml of cAMP buffer (DMEM (pH 7.4) containing 2 mM 3-isobutyl-methylxanthine, 1 mg/ml BSA and 35 mM HEPES). And then, 0.1 ml of cAMP buffer was added to the plate, and 0.1 ml of cAMP buffer containing each hormone of various concentration was added. Then, reaction was at 37° C. for 20 minutes and the buffer was removed. And then, freezing at −70° C. and thawing at room temperature were repeated three times for 20 minutes, respectively, to destruct the cells, and 1 ml of 50 mM HCl was added to each well of the plate. Then, intracellular cAMP was extracted at −20° C. for 16 to 18 hours, and quantitation of cAMP in the extract was carried out by using cAMP RIA kit (New England Nuclear, Du Pont, USA). Optimization of curve and $EC_{50}$ (concentration of hormone required for stimulating production of intracellular cAMP to reach an increase of 50%) were determined according to fig.P program of Biosoft Co. $EC_{50}$ values of shPTH (1–84) and rhPTH (1–84) were 1.9±0.1 and 1.3±0.2 mM (the average value±the standard deviation), respectively. One of the results was shown in FIG. 18(B). As shown in FIG. 18(B), it was found that the recombinant PTH had the same activity stimulating adenylate cyclase as the synthetic PTH.

As clearly illustrated and demonstrated as aboves, the present invention provides a recombinant expression vector which is prepared by inserting a human PTH gene containing an urokinase-specific cleavage site into a L-arabinose inducible vector containing a PRK gene fragment, a recombinant microorganism translated with the said expression vector or its mutated gene as a fusion partner, and a process for preparing human PTH on a large scale by cultivating the said microorganism in a medium containing L-arabinose. In accordance with the invention, a recombinant human PTH having the same activity of the native human PTH can be prepared in a high yield through the precise control of induction by a manufacturing process which comprises a step of inducing expression of fusion protein in the microorganism transformed with the recombinant expression vector by L-arabinose.

What is claimed is:

1. A recombinant expression vector which is prepared by inserting a human parathyroid hormone gene comprising a urokinase-specific cleavage site into an L-arabinose inducible vector comprising, as a fusion partner to said human parathyroid hormone gene, a phosphoribulokinase gene fragment of *Rhodobacter sphaeroides* or a gene fragment encoding a mutated phosphoribulokinase, said mutated phosphoribulokinase comprising mutations in which the $30^{th}$, $58^{th}$ and $94^{th}$ arginine residues are substituted with valine residues and the $59^{th}$ and $96^{th}$ arginine residues are substituted with glycine residues.

2. The recombinant expression vector of claim 1, wherein the L-arabinose inducible vector containing a phosphoribulokinase (PRK) gene is pPRK whose gene map is shown in FIG. 4.

3. The recombinant expression vector of claim 1, wherein the phosphoribulokinase gene fragment is a DNA fragment coding for 113 to 153 amino acids from amino-terminus of phosphoribulokinase.

4. The recombinant expression vector of claim 1, wherein the urokinase-specific cleavage site is a DNA sequence deducible from the following amino acid sequence:

-X-Gly-Arg wherein,

X is Pro, Thr, Ile, Phe or Leu.

5. The recombinant expression vector of claim 1, wherein the urokinase-specific cleavage site is a DNA sequence deducible from an amino acid sequence of -Thr-Gly-Arg.

6. The recombinant expression vector of claim 1, wherein the human parathyroid hormone gene has the following DNA sequence (SEQ ID NO:26):

TCT GTT TCG GAA ATC CAG CTT ATG CAT AAC CTG GGT AAA 39

CAT CTG AAC TCG ATG GAA CGT GTT GAA TGG CTG CGT AAA 78

AAA CTG CAG GAT GTT CAT AAC TTC GTT GCG CTG GGG GCT 117

CCA CTG GCG CCG CGC GAG GCG GGT TCG CAG CGC CCA CGT 156

AAA AAG GAA GAT AAC GTT CTG GTA GAG TCG CAT GAA AAG 195

TCT CTT GGC GAG GCT GAT AAA GCA GAC GTA GAC GTT TTG 234

ACT AAA GCA AAA TCT CAA TAA TGA 258.

7. A recombinant expression vector p153PTH which contains: a DNA fragment coding for 153 amino acids from amino-terminus of phosphoribulokinase of *Rhodobacter sphaeroides;* a DNA fragment coding for a urokinase-specific cleavage site of -Thr-Gly-Arg; and, a human parathyroid hormone gene.

8. The recombinant expression vector which contained the following genes in a serial manner: a DNA fragment coding for 153 amino acids from the amino-terminus of phosphoribulokinase of *Rhodobacter sphaeroides*, in which the arginine residues located at the $30^{th}$, $31^{th}$, $58^{th}$, $59^{th}$, $94^{th}$ and $96^{th}$ positions are substituted with different amino acids; a DNA fragment coding for a urokinase-specific cleavage site of X-Gly-Arg (wherein, X is Pro, Thr, Ile, Phe or Leu); and, a human parathyroid horomone gene.

9. A recombinant expression vector pm153PTH which contains the following genes in a serial manner: a DNA fragment coding for 153 amino acids from amino-terminus of phosphoribulokinase of *Rhodobacter sphaeroides* whose 30th, 58th, and 94th arginine residues are site-specifically mutated to be substituted with valines and 59th and 96th arginine residues with glycines; a DNA fragment coding for a urokinase-specific cleavage site of -Thr-Gly-Arg; and, a human parathyroid hormone gene.

10. *Escherichia coli* MC1061:p153PTH (KCCM-10101) transformed with the recombinant expression vector p153PTH of claim 7.

11. *Escherichia coli* MC1061:pm153PTH (KCCM-10102) transformed with the recombinant expression vector pm153PTH of claim 9.

12. A process for preparing a human parathyroid hormone which comprises the steps of: cultivating *Escherichia coli* MC1061:p153PTH (KCCM-10101); inducing the expression of a human parathyroid hormone by L-arabinose; and, recovering the human parathyroid hormone.

13. A process for preparing a human parathyroid hormone which comprises the steps of: cultivating *Escherichia coli* MC1061:pm153PTH (KCCM-10102); inducing the expression of a human parathyroid hormone by L-arabinose; and, recovering the human parathyroid hormone.

14. A process for preparing a human parathyroid hormone which comprises the steps of: cultivating a recombinant microorganism transformed with the recombinant expression vector of claim 1; inducing the expression of a human parathyroid hormone by L-arabinose; treating the expressed fusion protein of phosphoribulokinase and a human parathyroid hormone with urokinase to recover the human parathyroid hormone.

* * * * *